United States Patent [19]

Miketi et al.

[11] Patent Number: 4,708,125
[45] Date of Patent: Nov. 24, 1987

[54] APPARATUS FOR CONTROLLING A PROBE OF AN ENDOSCOPY DEVICE

[75] Inventors: Sinisa Miketi; Udo Schade, both of Kassel; Michael Schade, Solingen, all of Fed. Rep. of Germany

[73] Assignee: Messrs. Karl Storz GmbH & Co., Fed. Rep. of Germany

[21] Appl. No.: 887,631

[22] Filed: Jul. 21, 1986

[30] Foreign Application Priority Data

Jul. 24, 1985 [DE] Fed. Rep. of Germany ....... 3526434

[51] Int. Cl.⁴ .............................................. A61B 1/00
[52] U.S. Cl. ..................................................... 128/4
[58] Field of Search ......................... 128/4, 6; 433/101

[56] References Cited

U.S. PATENT DOCUMENTS 4,114,275  9/1978  Jones .................................... 433/101
4,256,998  3/1981  Samuels et al. ................. 433/101 X
4,265,622  5/1981  Hasegawa ........................... 433/101
4,539,586  9/1985  Danna et al. ....................... 128/6 X Primary Examiner—William H. Grieb

[57] ABSTRACT

The apparatus according to the invention for controlling a probe which has a sheathing of an endoscopy device, serves for eliminating difficulties in regard to co-ordination between the doctor operating the endoscopy device and the assistant who is operating the probe. At its one end, the probe has a movable medical instrument (10) while at its other end it has an operating member (8). For the purposes of controlling the probe, the apparatus is provided with a receiving means (5) for the probe sheathing (6), an actuating element (9), a drive unit for controlling the probe function and foot switches (23a, 23b) for controlling the control function. For the specific situation of an injection probe the apparatus has a further functional unit with suitable drive and fixing means (34, 35 and 12 respectively) for pressing out a medical hypodermic syringe (11,12) which is connected to the injection probe.

11 Claims, 7 Drawing Figures

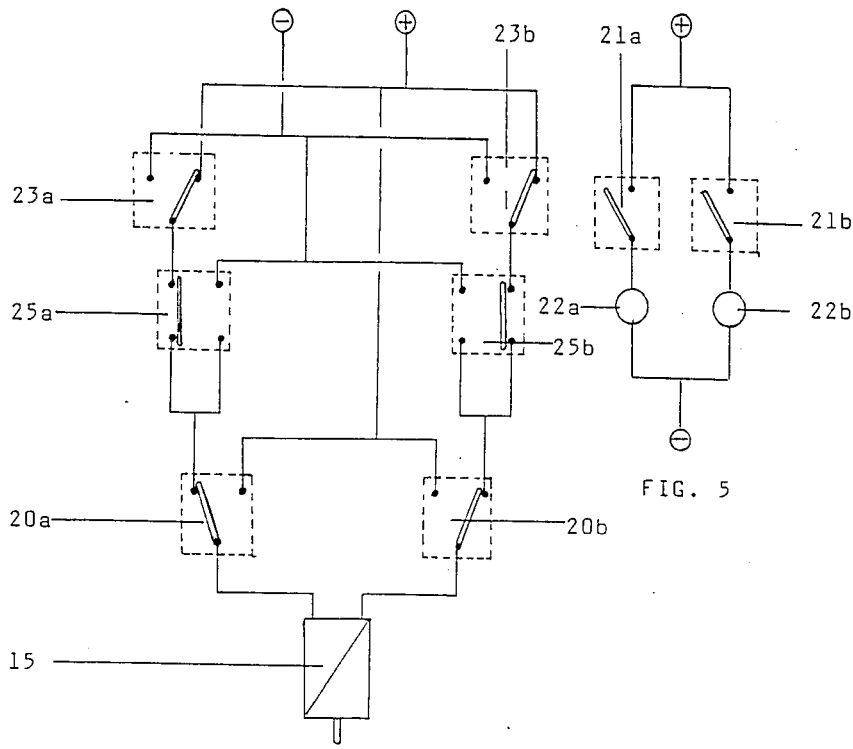
FIG. 4
FIG. 5
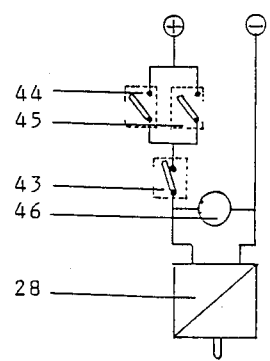
FIG. 6

APPARATUS FOR CONTROLLING A PROBE OF AN ENDOSCOPY DEVICE

The invention relates to an apparatus for controlling a probe, which has a sheathing, of an endoscopy device, wherein at its one end the probe has a movable medical instrument while at its other end it has an operating member, and also has an actuating element which extends through the sheathing and which is connected to the operating member and the instrument.

The use of known endoscopes, in particular fibrescopes, involves a considerable amount of expenditure and many difficulties. When carrying out the operation for endoscopic removal of varicose veins in the oesophagus for example the doctor operating the endoscopy device must operate the optical system with one hand, position the front end of the probe with the other hand and at the same time use his eyes to observe and monitor the positioning of the equipment. He therefore requires an assistant who on his instruction moves backwards and forwards the hypodermic needle which is fixed to one end of the probe, and actuates a hypodermic syringe which is connected thereto. Finally a second assistant must guide the endoscopy tube surrounding the probe into the oesophagus of the patient and move it backwards and forwards therein, under the instructions from the doctor. By virtue of the resulting difficulties in co-ordination between the doctor and the two assistants, treatment for a varicose vein frequently cannot be carried out in the desired short time and with the necessary degree of precision, to the detriment of the patient. Furthermore, the procedure requires a large number of operating personnel.

Similar problems arise when using conventional endoscopy devices for other purposes and with other probes, for example those which, instead of the hypodermic needle, have another medical instrument in the form of a gripper, a coagulation loop or tie, a biopsy tong instrument or the like.

The present invention is based on the problem of so designing the apparatus as set forth in the opening part of this specification, that the doctor who is carrying out the removal operation can undertake control of the probe alone so that as a result not only is there a saving of one assistant but also a substantial improvement in the level of control accuracy is achieved.

To solve that problem, the invention is characterised by a housing, a first receiving means fixed thereto for securing the sheathing, a slide which is mounted displaceably in opposite directions in the housing, a second receiving means which is fixed to the slide for securing the operating member, a first drive means mounted in the housing for automatically displacing the slide in both directions and a switching means for selectively switching on the drive means in one direction or the other.

The present invention provides the advantage that control of the probe can be effected substantially automatically. The doctor only needs to operate the switching means. The switching means preferably has switches which can be easily reached by the doctor, for example a foot-actuable double switch, so that it can be actuated by the doctor without the doctor having to take his hands off the endoscopy device. By virtue of that arrangement, on the one hand the assistant for controlling the probe becomes unnecessary while on the other hand the control operation can be made easier and more precise.

Other advantageous features of the invention are set forth in the subsidiary claims.

The invention will now be described in greater detail by means of two embodiments with reference to the accompanying drawings in which:

FIG. 4 shows a protective circuit for controlling the extension and retraction movement of the hypodermic needle of the probe;

FIG. 5 shows a circuit for controlling telltale lamps which indicate the end of the stroke movement of the slide;

FIG. 6 shows a circuit for controlling a slider for the actuation of a hypodermic syringe which is connected to the injection probe.

Figure 1:
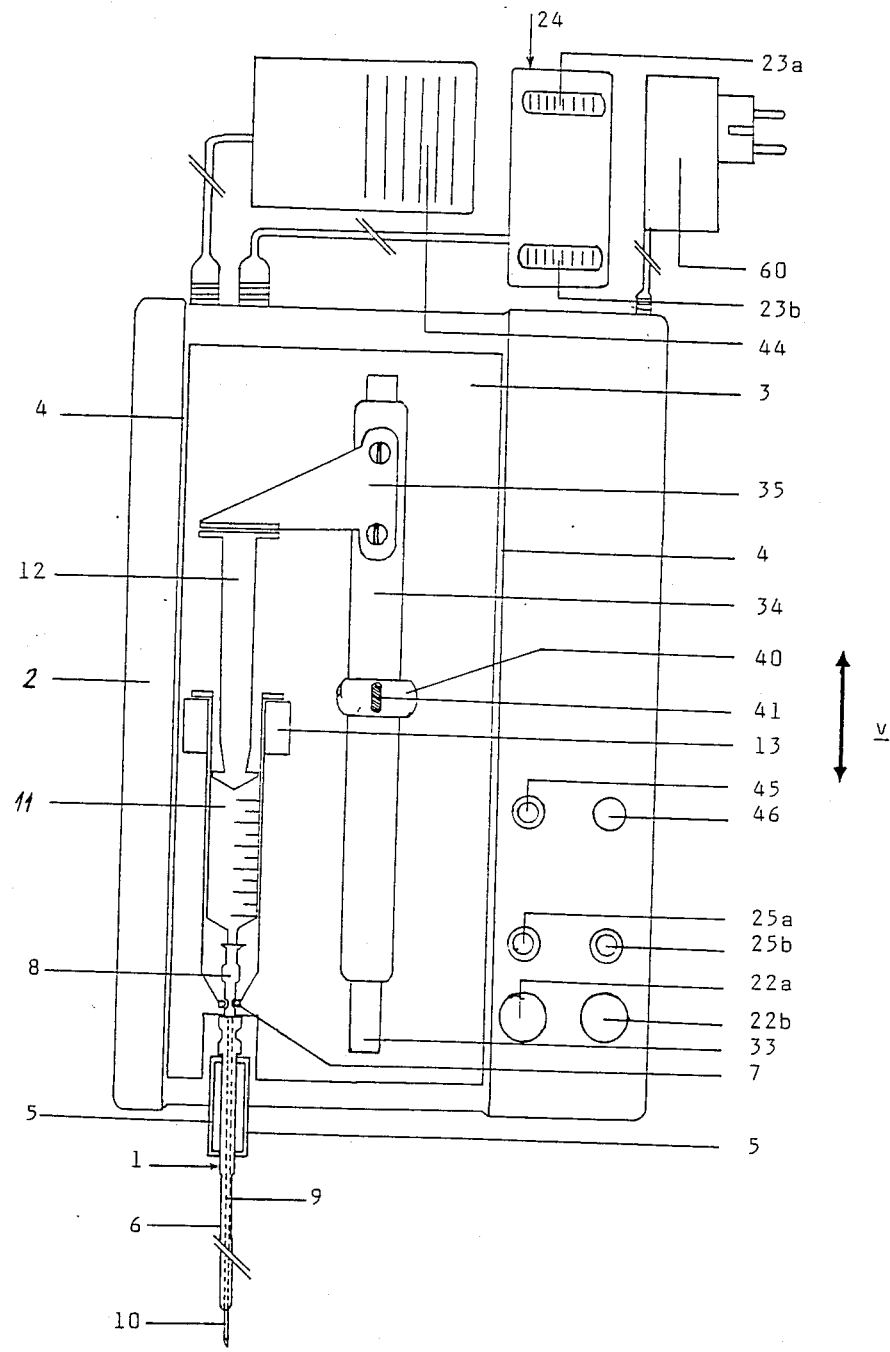
FIG. 1 is a plan view of an apparatus according to the invention for controlling the injection probe of an endoscopy device.

The apparatus according to the invention for controlling an injection probe 1 of an endoscopy device has a housing 2, on the top side of which a slide or carriage 3 is mounted displaceably in guides 4. In that arrangement the slide 3 can be reciprocated in the direction indicated by a double-headed arrow at v. A first receiving means 5 is fixed to a front part of the housing 2 and serves for for example clampingly receiving and securing a part of a casing or sheathing 6 of the injection probe 1. Secured to the slide 3 is a second receiving means 7 which is coaxial with respect to the first receiving means 5 and which serves for example for clampingly receiving and securing an operating member 8 of the injection probe 1. Extending through the sheathing 6 of the injection probe 1 is an actuating element 9 having an end portion which projects out of the one end of the sheathing 6 and which is connected to the operating member 8. The other end portion of the actuating element 9 carries a medical instrument in the form of a hypodermic needle 10 which, by means of the actuating element 9, can be retracted into the front end of the sheathing 6 or urged outwardly out of the front end of the sheathing 6. The actuating element 9 acts in the manner of a Bowden cable which is actuated by means of the operating member 8 and in this case is hollow. The operating member 8 is also hollow and has a connection for the reduced end of a cylinder 11 in which a piston 12 is mounted for reciprocating movement therein. In conjunction with the cylinder 11, the piston 12 represents a medical syringe. For the purposes of holding the syringe to the slide 3, the slide 3 has a third receiving means 13 which is operative for example by a clamping action and in which the cylinder 11 can be secured. The receiving means 13 is disposed on the side of the second receiving means 7, which is remote from the first receiving means 5, and extends coaxially with respect to the receiving means 5 and 7.

Figure 3:
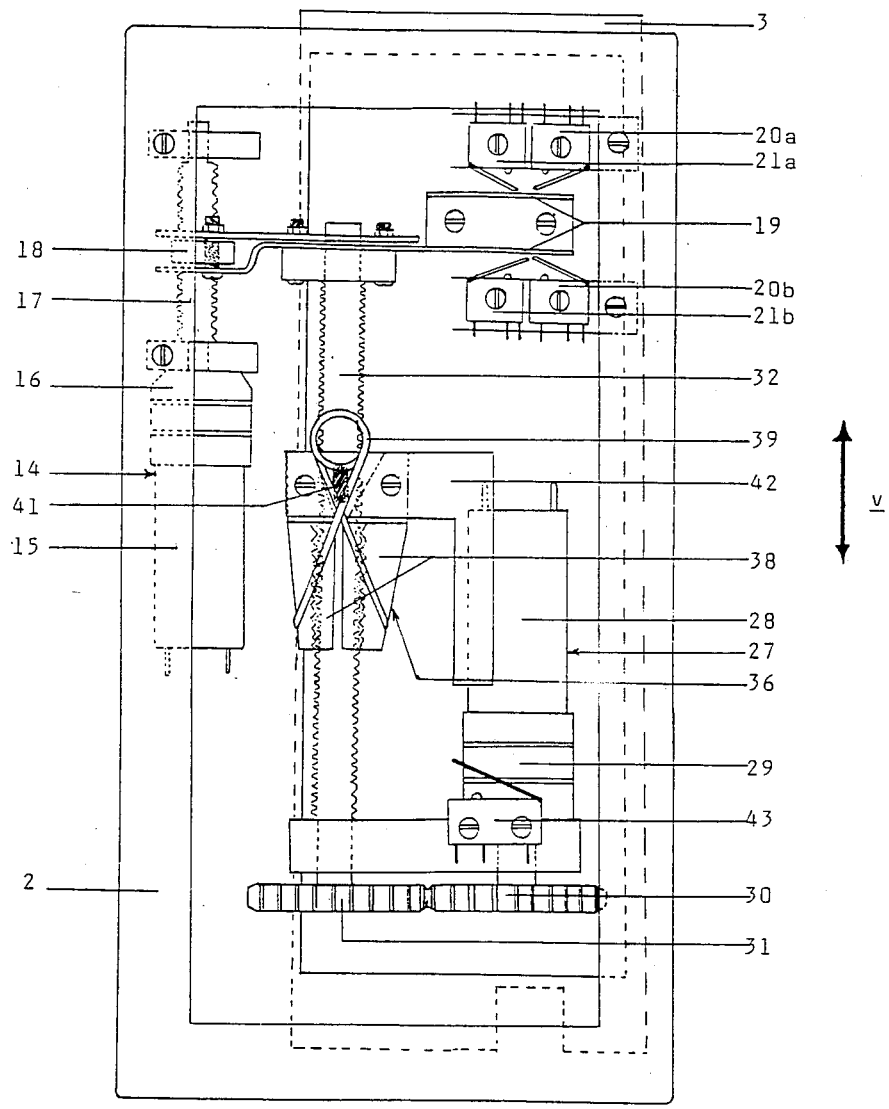
FIG. 3 is a view from below of the entire apparatus shown in FIG. 1.

As shown in FIG. 3, a first drive unit 14 is disposed in a lower part of the housing 2. The drive unit 14 comprises a reversible motor 15 which is secured to the housing 2 and whose output shaft, by way of a reducing transmission 16, can rotate a screwthreaded bar 17 which is mounted rotatably in the housing. Fitted on to the screwthreaded bar 17 is a screwthreaded nut 18 having an arm 19 which extends radially away therefrom and which is connected to the slide 3. In that way, the rotary movement of the screwthreaded bar 17, which is produced when the reversible motor 15 is switched on selectively in one direction of rotation or the other is converted into a linear reciprocating movement of the slide 3 parallel to the double-headed arrow v.

The arm 19 is disposed between two pairs of limit switches 20a, b and 21a, b, the pairs being spaced in the direction indicated by the double-headed arrow v. The limit switches 20a, b fix the stroke movement of the slide 3 in the direction indicated by the double-headed arrow v insofar as they are connected into a circuit of the reversible motor 15 so that, after having been switched on, the motor is automatically switched off in each case and thus the slide 3 is stopped, when the arm 19 comes into abutment against one of the limit switches 20a, b. In that connection the stroke movement of the slide 3 is so selected that it precisely corresponds to the maximum travel required for extension and retraction respectively of the hypodermic needle 10. The correspondingly arranged limit switches 21a, b are each associated with a telltale lamp 22a, b (see FIG. 1) which is disposed on the top surface of the housing and which lights up as soon as the slide 3 has reached its corresponding limit position. After that limit position has been reached, the reversible motor 15 can be switched on in the respectively opposite direction of rotation.

After the injection probe 1 has been secured in the receiving means 5 and 7, the above-described apparatus permits the hypodermic needle 10 to be retracted and extended in motorised mode by selectively switching on the reversible motor 15 in one direction of rotation or the other. In order to afford the doctor who is operating the endoscopy device which in other respects is known and is therefore not illustrated in greater detail the option of also carrying out himself the necessary switching operations for controlling the reversible motor 15, the circuit thereof advantageously includes two switches 23a, b which are to be operated by the foot and which are combined for example to form a double switch 24. Alternatively, the arrangement could employ switches which are so arranged on the endoscopy device that the doctor can easily reach them with a free finger or the like. Finally, the circuit of the reversible motor 15 could also include two manual switches 25a, b which carry out the same functions as the switches 23a, b and which thus permit an operating check to be carried out before the apparatus is put into operation.

Figure 2:
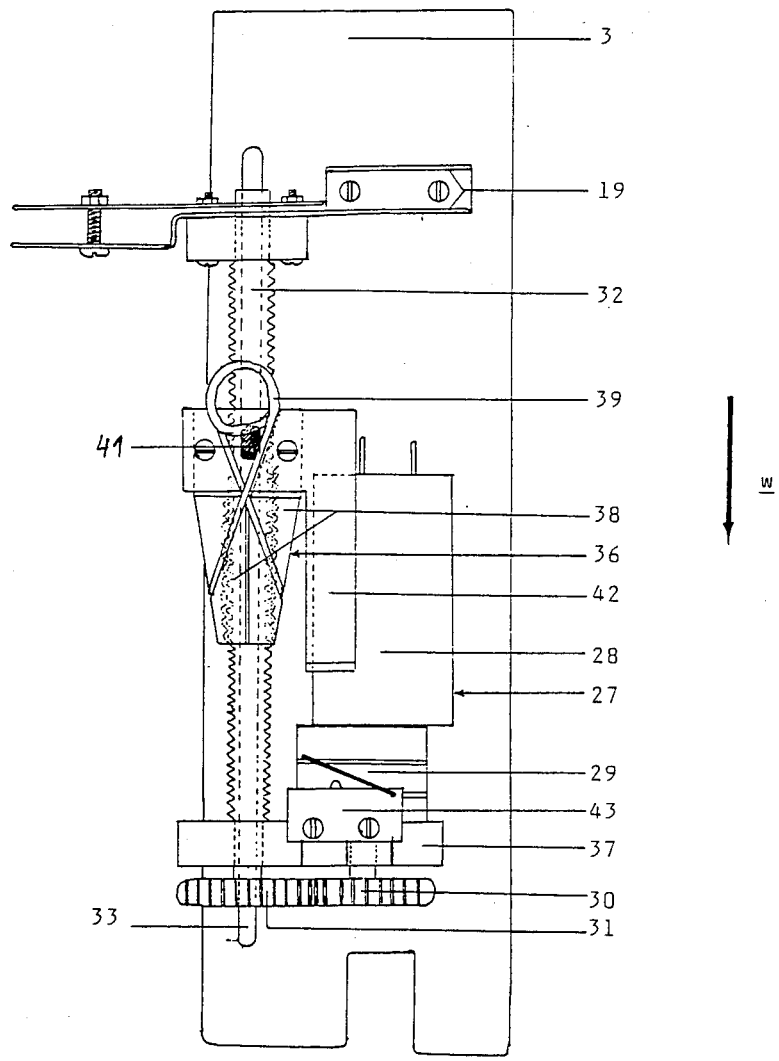
FIG. 2 is a view from below of a movable slide of the apparatus shown in FIG. 1.

As shown in particular in FIGS. 2 and 3, a second drive device 27 is provided for further control of the injection probe 1. The second drive device 27 is also disposed in a lower part of the housing 2. The drive device 27 includes a motor 28 whose output shaft is connected by way of a second reducing transmission 29 to a gear 30 which meshes with a second gear 31 to which a second screwthreaded bar 32 is fixed. The screwthreaded bar 32 is mounted rotatably on the slide 3. The axes of rotation of all those components are parallel to the direction indicated by the double arrow v. Provided on the top side of the slide 3 is a slot-type guide 33 which is parallel to the double-headed arrow v and in which a slider 34 is mounted for reciprocating movement therein. The slider 34 has an arm 35 which projects laterally away therefrom and which engages over the piston 12 of the injection probe 1 and which provides for displacement of the piston 12. Moreover, the slider 34 is connected to a screwthreaded sleeve 36 which is drawn on to the second screwthreaded bar 32 so that, when the motor 28 is switched on, the slider is displaced with a movement parallel to the double-headed arrow v, by way of the gears 30 and 31 and the screwthreaded bar 32. The entire second drive device 27 is carried by a mounting block 37 which is secured to the slide 3 so that it also moves as a unit with the slide.

The motor 28 could in principle also be a reversible motor and could be controlled in a similar manner to the reversible motor 15. In order to simplify replacement or fitting of the syringe 11 and 12 however the motor 28 is only a motor which rotates in one direction (arrow w in FIG. 2) and which can be disconnected from the slider 34 by a coupling means which is connected between the motor 28 and the slider 34. The coupling means is provided for example by the screwthreaded sleeve 36 being made up of two half-shells 38 which are held together by a spring 39. For the purposes of actuation of the coupling means, provided on the top side of the slider 34 is a rotary knob 40 which on its rear side has a spreading element 41 which projects through the slot-type guide 33 and which is disposed between the two half-shells 38. In that way it is possible for the two half-shells 38 to be moved apart from each other, against the pressure of the spring 39, by actuation of the rotary knob 40, to such a degree that the two half-shells are thereby disconnected from the screwthreaded bar 32 and the slider 34 can be reciprocated between its limit positions, by hand. That permits the slider 34 to be coupled to the screwthreaded bar 32 at any desired position thereon, in order for example to be able to adjust the arm 35 to syringes of different lengths.

Secured to the screwthreaded sleeve 36 is a projection 42, while a limit switch 43 which is secured to the mounting block 37 is associated with the projection 42. That limit switch 43 fixes the travel movement of the slider 34 in the direction indicated by the arrow w, that movement precisely corresponding to the travel of the piston 12 in the cylinder 11 of the syringe. For that purpose, the limit switch 43 is connected into a circuit of the motor 28 which can also be switched on and off by means of a further foot switch 44. Moreover, for the purposes of operational checking of the motor 28, the arrangement includes a hand switch 45 which is disposed on the top side of the housing 2 and which performs the same function as the foot switch 44, and a telltale lamp 46 which lights up only when the motor 28 is running and which, together with the hand switch 43, is also connected into the circuit of the motor 28.

The mode of operation of the described apparatus is as follows:

After the sheathing 6 of the injection probe 1 has been fixed in the receiving means 5 and the operating member 8 has been fixed in the receiving means 7, an e.g. empty syringe which has been extended and connected to the operating member 8 can be laid into the receiving means 13. The slider 34 is then disconnected from the motor 28 by actuation of the rotary knob 40 and displaced by hand in such a way that the arm 35 bears against the end of the piston 12. Thereupon the slider 34 is reconnected to the motor 28 by fresh actuation of the rotary knob 40. Then, the various functions of the apparatus are checked by means of the hand switches 25a, b and 45 or, after connection of the foot switches 23a, b and 44, also with those switches, the telltale lamps indicating in each case the respectively associated function. Finally the slider 34 is brought back again and the empty syringe is replaced by a filled syringe with the piston extended.

Figure 7:
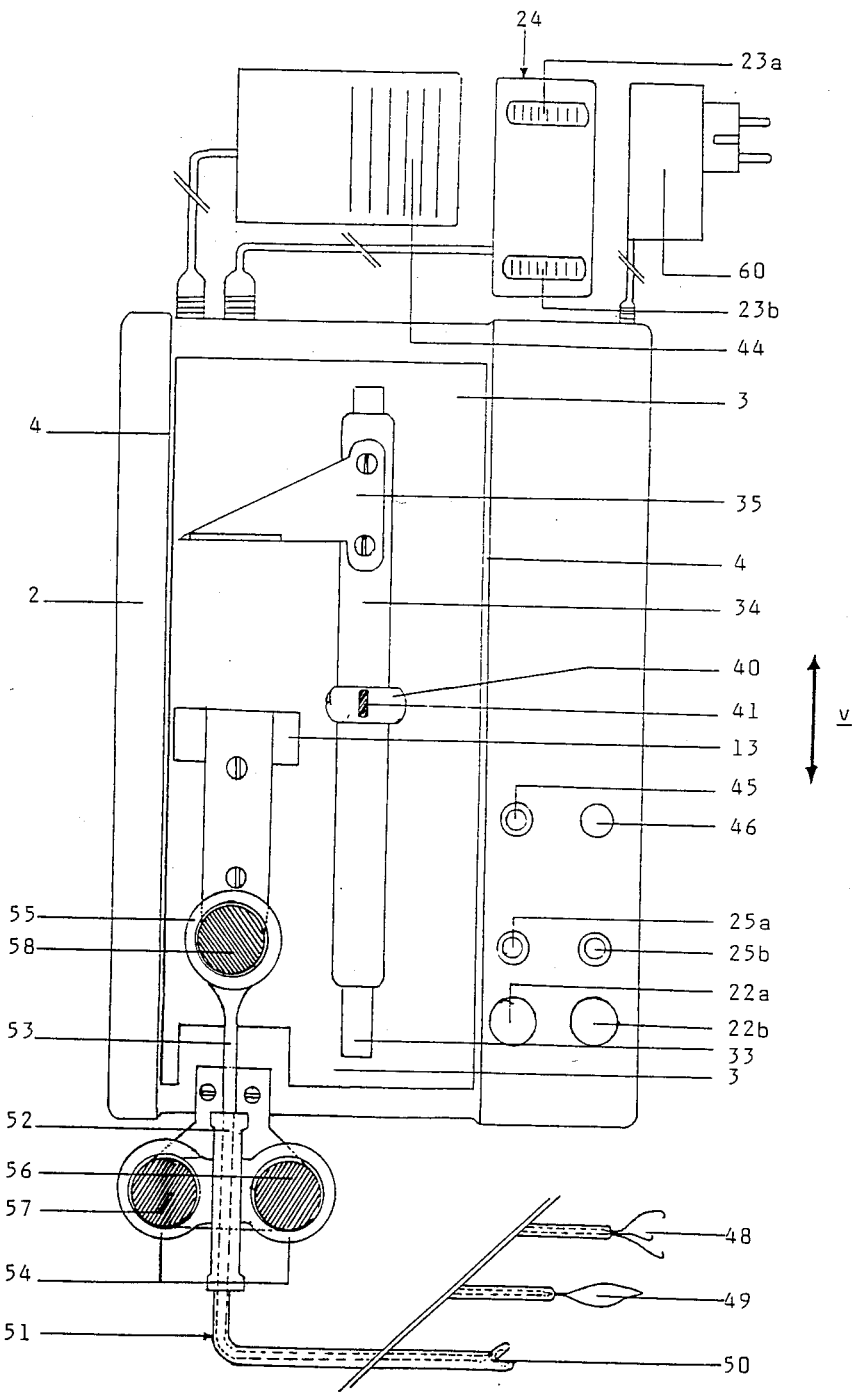
FIG. 7 is a plan view of the apparatus shown in FIG. 1 in relation to controlling altenrative endoscopy probes.

FIG. 7 in which like components are identified by like references shows use of the described apparatus for other endoscopy processes, for example those in which a probe is used with another medical instrument, for example a gripper 48, a coagulation loop or tie 49 or a biopsy tong instrument 50. Each of those probes has a sheathing or casing 51 in which an actuating element 52 is arranged in the manner of a Bowden cable or the like; one end portion of the actuating element 52, which projects out of the rearward end of the sheathing 51, is secured to an operating element 53, while the other end portion of the actuating element 52 is used in known manner for actuating that instrument, for example the gripper 48, the coagulation loop or tie 49 or the biopsy tong instrument 50, which is arranged movably at the forward end of the probe. For the purposes of actuation of such probes, use is normally made of two rings 54 which are arranged rigidly relative to the sheathing 51, for receiving the index and middle fingers of one hand, and a ring 55 which is secured to the operating element 53 for receiving the thumb of the same hand, for actuation of the respective medical instrument used. As hitherto, when using such probes, actuation of the instruments can only be effected by an assistant, the receiving means 5 and 7 of the apparatus shown in FIG. 1 are secured removably to the housing 2 and the slide 3 respectively. If an injection probe 1 other than that shown in FIG. 1 is required for the endoscopy device, those receiving means 5 and 7 can be dismantled and replaced by other receiving means 56, 57 and 58 which are suitable for example for clampingly mounting the rings 54 and 55 shown in FIG. 7, and thus securing the sheathing 51 to the housing 2 and the operating member 53 to the slide 3 respectively. If it should be necessary in such situations for the stroke movement of the slide 3, which is fixed by the limit switches 20a and b, to be matched to the probe provided in each individual situation, preferably at least one of the limit switches 20a, b is arranged displaceably or adjustably on an easily accessible point on the housing 2.

The reversible motor 15 and the motor 28 are preferably 12 V drive motors which are driven by way of a 220 V transformer 60 which for safety reasons is disposed outside the housing 2.

FIGS. 4, 5 and 6 diagrammatically show the circuitry of the drive units 15 and 28, the telltale lamps 22a, b and 46, the operating switches 23a, b, 25a, b, 44 and 45 and the limit switches 20a, b, 21a, b and 43 in corresponding electrical circuit arrangements.

In FIG. 4, the operating switches 23a, b and 25a, b are in the unactuated condition and the two limit switches 20a, b are in the closed condition so that both terminals of the reversible motor 15 are connected to the ⊕-line of the transformer 60. The motor 15 is therefore stationary. Upon actuation of one of the switches 23a, b or 25a, b on the other hand, one of the terminals of the reversible motor 15 is connected to the ⊖-line of the transformer 60, so that the reversible motor 15 rotates in one direction or the other. When, when a limit position is reached, the associated limit switch 20a, b is actuated, that in turn results in the corresponding terminal being connected to the ⊕-line so that the reversible motor 15 remains in the limit position until actuation in the opposite direction occurs, whereby the respective limit switch 20a, b returns to the position shown in FIG. 4, thereby restoring the starting position as shown in FIG. 4.

FIG. 5 shows that, at the same time as the limit switches 21a, b are switched over, the respective current paths which include the telltale lamps 22a, b, between the ⊕-line and the ⊖-line, are closed.

Referring to FIG. 6, therein the two terminals of the motor 28 are connected to the ⊕-line and the ⊖-line respectively; connected into one branch are the limit switch 43 and a parallel circuit which contains the foot switch 44 and the hand switch 45. When one of the switches 44, 45 is actuated therefore the motor 28 is energised while at the same time the telltale lamp 46 is lit. When the limit switch 43 opens, that results in the telltale lamp 46 being extinguished.

The invention is not restricted to the described embodiments which may be modified in many ways. That applies in particular in regard to the specific configuration, as selected in the illustrated embodiments, of the various receiving means, drive means and control means thereof.

We claim:

1. Apparatus for controlling a probe, which has a sheathing, of an endoscopy device, wherein at its one end the probe has a movable medical instrument while at its other end it has an operating member, and also has an actuating element which extends through the sheathing and which is connected to the operating member and the instrument, characterised by a housing (2), a first receiving means (5, 56, 57) fixed thereto for securing the sheathing (6), a slide (3) which is mounted displaceably in opposite directions in the housing (2), a second receiving means (7, 58) which is fixed to the slide (3) for securing the operating member (8, 53), a first drive means (14) mounted in the housing (2) for automatically displacing the slide (3) in both directions and a switching means (23a, b; 25a, b) for selectively switching on the drive means (14) in one direction or the other.

2. Apparatus according to claim 1 for control of an injection probe whose operating member is provided with a connection for a medical syringe having a piston and a cylinder, characterised in that fixed to the slide (3) are a third receiving means (13) for securing the cylinder (11) of the syringe and a second drive means (27) for actuation of the piston (12) of the syringe, wherein the second drive means (27) has a slider (34) mounted displaceably on the slide (3) and a switch (44, 45) for selectively switching on the drive means (27).

3. Apparatus according to claim 1 characterised in that the switching means has a double switch (24) which is to be actuated with the foot.

4. Apparatus according to claim 2 characterised in that the switch (44) is a switch which is to be actuated with the foot.

5. Apparatus according to claim 1 characterised in that the first drive means (14) comprises a first screwthreaded bar (17) which is mounted rotatably in the housing (2), a reversible motor (15) having an output shaft connected to the first screwthreaded bar (17) and a screwthreaded nut (18) which is fixed to the slide (3) and through which the first screwthreaded bar (17) extends.

6. Apparatus according to claim 2 characterised in that the second drive means (27) has a motor (28) for displacement of the slider (34) and a coupling means connected between said slider and the motor (28).

7. Apparatus according to claim 6 characterised in that the second drive means (27) has a second screwthreaded bar (32) which is mounted rotatably on the slide (3) and which is connected to the output shaft of the motor (28), and that the coupling means comprises a screwthreaded sleeve (36) which is fitted on to the second screwtheaded bar (32) and which comprises two half-shells (38) held together by a spring (39) and a rotary knob (40) mounted on the slider (34), the rotary knob carrying a spreading element (41) which projcts between the two half-shells (38).

8. Apparatus according to claim 5 characterised in that the screwthreaded nut (18) has a radially projecting arm (19) disposed between two limit switches (20a, b) which are fixed to the housing and which are at a spacing from each other which corresponds to the maximum admissible stroke movement of the slide (3) in the two mutually opposite directions.

9. Apparatus according to claim 8 characterised in that the arm (19) is disposed between two further limit switches (21a, b) which are fixed to the housing (2) and which are connected to telltale lamps (22a, b) indicating the limit positions of the slide (3).

10. Apparatus according to claim 7 or claim 8 characterised in that the second drive means (27) has a projection (42) which is secured to the screwthreaded sleeve (36), while associated with the projection (42) is a limit switch (43) which is fixed to the slide (3) and which delimits the end of the stroke movement of the slider (34).

11. Apparatus according to claim 7 or claim 8 characterised in that the two screwthreaded bars (17, 32) are arranged in mutually parallel relationship.

* * * * *